(12) United States Patent
Lee et al.

(10) Patent No.: US 7,571,847 B2
(45) Date of Patent: Aug. 11, 2009

(54) APPARATUS FOR MEASURING NUMBER OF FOOTSTEPS AND METHOD THEREOF

(75) Inventors: Woo-jong Lee, Suwon-si (KR); Sang-on Choi, Suwon-si (KR)

(73) Assignee: Samsung Electro-Mechanics Co., Ltd, Suwon-si (KR)

(*) Notice: Subject to any disclaimer, the term of this patent is extended or adjusted under 35 U.S.C. 154(b) by 645 days.

(21) Appl. No.: 11/251,887

(22) Filed: Oct. 18, 2005

(65) Prior Publication Data
US 2006/0111843 A1 May 25, 2006

(30) Foreign Application Priority Data
Nov. 19, 2004 (KR) .................. 10-2004-0094963

(51) Int. Cl.
*G01C 22/00* (2006.01)
(52) U.S. Cl. ..................... 235/105; 235/375
(58) Field of Classification Search ............ 235/375, 235/78 N, 88 N, 61 NV, 105; 702/160, 150
See application file for complete search history.

(56) References Cited

U.S. PATENT DOCUMENTS

| 5,065,414 | A | 11/1991 | Endou et al. |
| 6,546,336 | B1 | 4/2003 | Matsuoka et al. |
| 6,594,617 | B2 * | 7/2003 | Scherzinger ............ 702/160 |
| 2003/0080869 | A1 | 5/2003 | Pellet et al. |

FOREIGN PATENT DOCUMENTS

EP   0 908 701 A2   4/1999

* cited by examiner

*Primary Examiner*—Karl D. Frech
(74) *Attorney, Agent, or Firm*—Sughrue Mion, PLLC

(57) ABSTRACT

A footstep measuring apparatus and a method thereof are provided. The apparatus includes: a terrestrial magnetism sensor for outputting digital values of each axis according to movements of a body; a reference digital value generator for generating a reference digital value based on N digital values of each axis, (N−1) digital values of each axis, (N−2) digital values of each axis; a reference axis selector for searching N digital value of one axis having a maximum amplitude and selecting the one axis as a reference axis; a digital value determiner for determining whether the N digital value is larger than a reference digital value; and a controller for determining the movement as an ascending movement of one footstep when the N digital value is larger than the reference digital value.

22 Claims, 5 Drawing Sheets

APPARATUS FOR MEASURING NUMBER OF FOOTSTEPS AND METHOD THEREOF

CROSS-REFERENCE TO RELATED APPLICATIONS

This application claims priority from Korean Patent Application No. 2004-94963, filed on Nov. 19, 2004, in the Korean Intellectual Property Office, the entire disclosure of which is incorporated herein by reference.

BACKGROUND OF THE INVENTION

1. Field of the Invention

Apparatuses and methods consistent with the present invention relate to measuring a number of footsteps; more particularly, to measuring the number of footsteps using a terrestrial magnetism sensor.

2. Description of the Related Art

According to a growing interest in promoting health, footstep measuring apparatuses have been introduced and actively developed. For example, a handheld phone has been introduced that includes a function of measuring the number of footsteps, which has become very popular among people who want to preserve their health.

Conventional footstep measuring apparatuses generally use an acceleration sensor to measure the number of footsteps, and because of the acceleration sensor, the conventional footstep measuring apparatus consumes relatively large quantity of electric power.

Footstep measuring apparatuses are generally embedded in a small sized electric appliance such as a handheld phone. However, it is not preferable to embed the acceleration sensor, which consumes mass amounts of electric power, in such a small sized electric appliance having a limited electric power source.

SUMMARY OF THE INVENTION

An aspect of the present general inventive concept is to provide an apparatus and method for measuring the number of footsteps using a terrestrial magnetism.

It is another aspect of the present invention to provide an apparatus and method for measuring the number of footsteps by calculating a predetermined weight applied reference digital value and detecting an ascending movement and a descending movement of one footstep through comparing the reference digital value and a digital value of a target object.

It is still another aspect of the present invention to provide an apparatus and method for measuring the number of footsteps by subtracting previous digital values of each axis from current digital values of each axis, adding the subtracting results of each axis and determining a half of one footstep when a sign of the adding result is changed.

In accordance with an aspect of the present invention, there is provided an apparatus for measuring the number of footsteps, including: a terrestrial magnetism sensing unit for outputting digital values of each axis with a predetermined sampling time interval by using at least two axis of terrestrial magnetism sensors among a X-axis, a Y-axis and a Z-axis according to movements of a body; a reference digital value generator for generating a reference digital value based on N digital values of each axis output from the terrestrial magnetism sensing unit, (N−1) digital values of each axis output from the terrestrial magnetism sensing unit in one sampling time interval before the N digital values are output, (N−2) digital values of each axis output from the terrestrial magnetism sensor in one sampling time interval before the (N−1) digital values output; a reference axis selector for searching N digital value of one axis having a maximum amplitude in a predetermined period among the N digital values of each axis and selecting the one axis having the maximum amplitude as a reference axis; a digital value determiner for determining whether the N digital value of the selected reference axis is larger than a reference digital value of the selected reference axis as much as a predetermined value; and a controller for determining the movement of the body as an ascending movement of one footstep when the N digital value is larger than the reference digital value as much as a predetermined value.

The reference digital value generator may generate the reference digital value (Ref_Value) based on an equation as: Ref_Value=a×N_RxF+b×(N−1)_RxF+c×(N−2)_RxF, where N_RxF is an N digital value, (N−1)_RxF is a (N−1) digital value, the (N−2)_RxF is a (N−2) digital value, a denotes a weight allocated at an N sampling point, b represents a weight allocated at the (N−1) sampling point and c denotes a weight allocated at the (N−2) sampling point.

The controller may determine that the movement of the body is a descending movement of one footstep when the digital value determiner determines that the N digital value of the reference axis is smaller than the reference digital value of the reference axis as much as a predetermined value.

The apparatus may further include a counter for increasing the number of footsteps by one when the controller determines the descending movement.

The apparatus may farther include a display which displays the number of footsteps counted by the counter in response to the controller.

In accordance with another aspect of the present invention, there is provided an apparatus for measuring the number of footsteps including: a terrestrial magnetism sensing unit for outputting digital values of each axis within a predetermined sampling time by using at least two axis of terrestrial magnetism sensor among a X-axis, a Y-axis and a Z-axis according to movements of a body; a subtracter for generating difference digital values of each axis by subtracting (N−1) digital values of each axis, which are output in one sampling time before outputting N digital values of each axis from the terrestrial magnetism sensing unit, from the N digital values of each axis; an adder for generating a sum digital value by adding the difference values of each axis; and a controller for determining that the movement of the user is a half of one footstep when a sign of the sum digital value is changed.

The controller may determine that the movement of the body is another half of one footstep when the changed sign of the sum digital value is changed again.

The apparatus may further include a counter for increasing the number of footsteps by one when the controller determines that the movement of the body is another half of one step.

The apparatus may further include a display which displays the number of footsteps counted by the counter in response to the controller.

In accordance with still another aspect of the present invention, there is provided a method of measuring the number of footsteps, including: outputting digital values of each axis within a predetermined sampling time interval by using at least two-axis of terrestrial magnetism sensor among a X-axis, a Y-axis and a Z-axis according to movements of a body; generating a reference digital value based on N digital values of each axis, (N−1) digital values of each axis output in one sampling time before outputting the Nth digital values, (N−2) digital values of each axis output in one sampling time before outputting the (N−1) digital values; searching an N digital value of one axis having a maximum amplitude in a predetermined period among the N digital values of each axis and selecting the one axis as a reference axis; determining whether the N digital value of the selected reference axis is larger than a reference digital value of the selected reference axis as much as a predetermined value; and determining the movement of the body as an ascending movement of one footstep when the N digital value is larger than the reference digital value as much as a predetermined value.

In generating the reference digital value, the reference digital value (Ref_Value) may be generated based on an equation as Ref_Value=a×N_RxF+b×(N−1)_RxF+c×(N−2)_RxF, where N_RxF is an N digital value, (N−1)_RxF is a (N−1) digital value, the (N−2)_RxF is a (N−2) digital value, a denotes a weight allocated at an N sampling point, b represents a weight allocated at the (N−1) sampling point and c denotes a weight allocated at the (N−2) sampling point.

The method may further include: determining that the movement of the body is a descending movement of one footstep when the digital value determiner determines when the N digital value of the reference axis is a predetermined value smaller than the reference digital value of the reference axis.

The method may further include: increasing the number of footsteps by one when the controller determines the descending movement.

The method may further include: displaying the number of footsteps counted by the counter in response to the controller.

In accordance with further still another aspect of the present invention, there is provided a method for measuring the number of footsteps, including: outputting digital values of each axis within a predetermined sampling time interval by using at least two axis of terrestrial magnetism sensor among a X-axis, a Y-axis and a Z-axis according to movements of a body; generating difference digital values of each axis by subtracting (N−1) digital values of each axis, which are output in one sampling time before outputting N digital values of each axis, from the $N^{th}$ digital values of each axis; generating a sum digital value by adding the difference values of each axis; and determining that the movement of the user is a half of one footstep when a sign of the sum digital value is changed.

The method may further include determining that the movement of the body is another half of one footstep when the changed sign of the sum digital value is changed again.

The method may further include: increasing the number of footsteps by one when the controller determines that the movement of the body is another half of one step.

The method may further include: displaying the number of footsteps counted by the counter in response to the controller.

BRIEF DESCRIPTION OF THE DRAWINGS

The above and/or other aspects of the present invention will be more apparent by describing certain exemplary embodiments of the present invention with reference to the accompanying drawings, in which.

DETAILED DESCRIPTION OF EXEMPLARY EMBODIMENTS OF THE INVENTION

Exemplary embodiments of the present invention will be described in greater detail with reference to the accompanying drawings.

Figure 1:
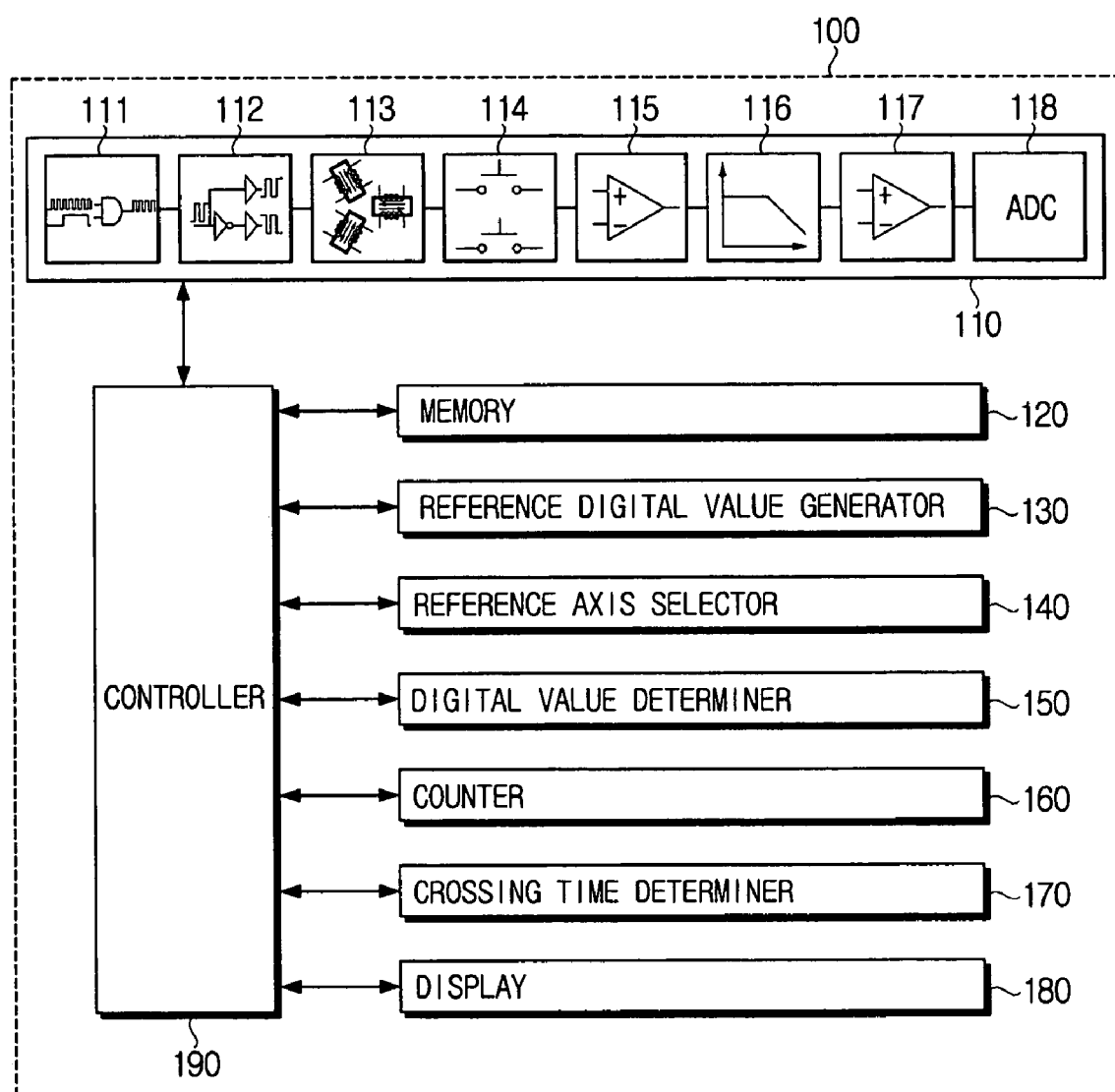
FIG. 1 is a block diagram illustrating an apparatus for measuring the number of footsteps according to an exemplary embodiment of the present invention.

In the following description, same drawing reference numerals are used for the same elements even in different drawings. FIG. 1 is a block diagram illustrating an apparatus for measuring the number of footsteps according to an exemplary embodiment of the present invention.

Referring to FIG. 1, an apparatus 100 for measuring the number of footsteps includes a terrestrial magnetism sensor 110, a memory 120, a reference digital value generator 130, a reference axis selector 140, a digital value determiner 150, a counter 160, a crossing time determiner 170, a display 180 and a controller 190.

The terrestrial magnetism sensor 110 outputs digital values of each axis including an x-axis digital value, a y-axis digital value, and a z-axis digital value, which represent a movement of user's body in response to the controller 190.

The terrestrial magnetism sensor 110 according to the present embodiment includes a operating pulse generating circuit 111, a current amplifying circuit 112, a three-axis fluxgate circuit 113, a chopping circuit 114, a first amplifying circuit 115, a lowpass filter 116, a second amplifying circuit 117 and an A/D converter 118. A two-axis fluxgate circuit may be used instead of using the three-axis fluxgate circuit 113 according to another exemplary embodiment of the present invention. However, in the present exemplary embodiment, the three-axis fluxgate circuit 113 is used for accurately detecting a movement of the user's body.

The operating pulse generating circuit 111 generates an operating pulse to operate the three-axis fluxgate 113. After generating the operating pulse, the operating pulse generating circuit 111 selectively switches the generated operating pulse and supplies the switched operating pulse to the current amplifying circuit 112.

The current amplifying circuit 112 generates a pulse signal and a reversed pulse signal having a reverse phase compared to the pulse signal based on the pulse output through the operating pulse generating circuit 111 by using a plurality of amplifiers and a reverser.

The three-axis fluxgate circuit 113 includes an X-axis fluxgate, a Y-axis fluxgate and a Z-axis fluxgate which are orthogonally crossed. The three-axis fluxgate circuit 113 generates a detection signal in response to an electromotive force generated by magnetic field generated by the pulse signal and the reverse pulse signal transferred to the X-axis fluxgate, the Y-axis fluxgate and the Z-axis fluxgate. Each of the X-axis fluxgate, the Y-axis fluxgate and the Z-axis fluxgate may include two rectangular ring-shaped magnetic substance cores which are arranged in a length direction based on each of X-axis, Y-axis and Z-axis. A driving coil and a sensing coil are wired at each of the magnetic substance cores. If the operating pulse is applied to the driving coil, the X-axis fluxgate, the Y-axis fluxgate and the Z-axis fluxgate generate a magnetic field, and the sensing coil senses an induced electromotive force according to the generated magnetic field.

The chopping circuit 114 chops an electric signal sensed from the three-axis fluxgate circuit 113 by using a plurality of switches. The first amplifying circuit 115 differentially amplifies the chopped electric signal and the lowpass filter 116 filters the chopped electric signal to generate signals within a predetermined range. The second amplifying circuit 117 finally amplifies the filtered signal. The A/D converter 118 converts the amplified signal to a digital value. That is, the A/D converter 118 outputs digital values of the X-axis, Y-axis and Z-axis in predetermined sampling time interval.

The memory 120 stores the digital values of each axis, i.e., X-axis digital values, the Y-axis digital value, and the Z-axis digital value output from the A/D converter 118 in response to the controller 190.

Hereinafter, digital values corresponding to the number of footsteps among the stored digital values are defined as a target digital value.

The reference digital value generating unit 130 generates a first reference digital value by using the stored digital value of the memory 120 such as an N digital value, a (N−1) digital value, a (N−2) digital value in response to the control of the controller 190. The N digital value, the (N−1) digital value and the (N−2) digital value represent digital values output from the A/D converter 118 within the sampling time interval. Among the output digital values, the N digital value is the target digital value.

The reference digital value generating unit 130 generates a second reference digital value by using digital values of X-axis, Y-axis and Z-axis stored in the memory 120 such as a (N+k+1) digital value, a (N+k+2) digital value and a (N+k+3) digital value, in response to the control of the controller 190. The (N+k+1) digital value, the (N+k+2) digital value and the (N+k+3) digital value represent digital values output from the A/D converter 118 within the sampling time interval. Also, a positive integer including 0 is applied to k and the (N+k+3) is the target digital value.

The reference digital value generating unit 130 may calculate the first reference digital value and the second reference digital value (Ref_Value) according to Equation 1, as follows:

$$\text{Ref\_Value} = a \times T\_RxF + b \times (T-1)\_RxF + c \times (T-2)\_RxF, \quad \text{Equation 1.}$$

In Equation 1, T_RxF is a T digital value of a time T and (T−1)_RxF is a (T−1) digital value of a time (T−1) which is one sampling time before the time T. Also, the (T−2)_RxF is a (T−2) digital value of a time (T−2) which is one sampling time before the time (T−1). Furthermore, in Equation 1, "a" denotes a weight allocated at the time T, "b" represents a weight allocated at the time (T−1) and "c" denotes a weight allocated at the time (T−2). A degree that a digital value of each time influences the reference digital value is determined according to the weight. A weight higher than a previous digital value may be applied by providing b and c to be larger than a.

The reference axis selector 140 analyzes digital values of each axis including the N digital value within a first predetermined period such as a X-axis digital value ($N_x$ digital value), a Y-axis digital value ($N_y$ digital value) and a Z-axis digital value ($N_z$ digital value) in response to the controller 190. The reference axis selector 140 also analyzes digital values of each axis including the (N+k+3) digital value within a second predetermined period such as a X-axis digital value ($(N+k+3)_x$ digital value), a Y-axis digital value ($(N+k+3)_y$ digital value) and a Z-axis digital value ($(N+k+3)_z$ digital value) in response to the controller 190. The first predetermined period and the second predetermined period may be optimally set by simulations.

The reference axis selector 140 searches a maximum value and a minimum value in the digital values of each axis. The reference axis selector 140 selects a reference axis having a maximum amplitude among the X-axis digital value, the Y-axis digital value and the Z-axis digital value. Hereinafter, a reference axis corresponding to the N digital value is defined as a first reference axis and a reference axis corresponding to the (N+k+3) digital value is defined as a second reference axis.

The digital value determiner 150 compares a reference digital value corresponding to the first reference axis and an N digital value corresponding to the first reference axis in response to the controller 190. If the first reference digital value is larger than the N digital value as much as a first predetermined value, the controller 190 indicates that an over-crossing has occurred. The term "over-crossing" means that a target digital value is larger than the reference digital value by a predetermined value. The first predetermined value is a value set by applying various experimental noises.

The digital value determiner 150 compares a second reference digital value corresponding to the second reference axis and a (N+k+3) digital value corresponding to the second reference axis in response to the controller 190 after detecting an ascending movement of one footstep. If the second reference digital value is larger than the (N+k+3) digital value by a second predetermined value, the controller 190 indicates that an under-crossing has occurred. The term "under-crossing" means that the target digital value is smaller than the reference digital value by a predetermined value. The second predetermined value is also set by applying experimental various noises.

The counter 160 increases the number of over-crossing by one when the over-crossing has occurred in response to the controller 190. The counter 160 also increases the number of under-crossing by one when the under-crossing has occurred in response to the controller 190.

The counter 160 also increase the number of footsteps by one when the ascending movement and the descending movement of one footstep are detected.

The crossing time determiner 170 determines whether the number of the over-crossing counted by the counter 160 is larger than a reference over-crossing time in response to the controller 190. The reference over-crossing time is set by applying various experimental noises. The reference over-crossing time may be 2, for example. If the increased over-crossing time is larger than the reference over-crossing time, the controller 190 determines that a body movement of a user is an ascending movement of one footstep.

The crossing time determiner 170 also determines whether the number of the under-crossing counted by the counter 160 is larger than a reference under-crossing time in response to the controller 190. The reference under-crossing time is set by applying various experimental noises. The reference under-crossing time may be 3, for example. If the increased over-crossing time is larger than the reference under-crossing time, the controller 190 determines that a body movement of a user is a descending movement of one footstep.

The display 180 displays the increased number of footsteps in response to the controller 190 when the counter 160 increases the number of footsteps by one.

The controller 190 generally controls the apparatus 100 for measuring the number of footsteps according to a control program stored in the memory 120.

Figure 2:
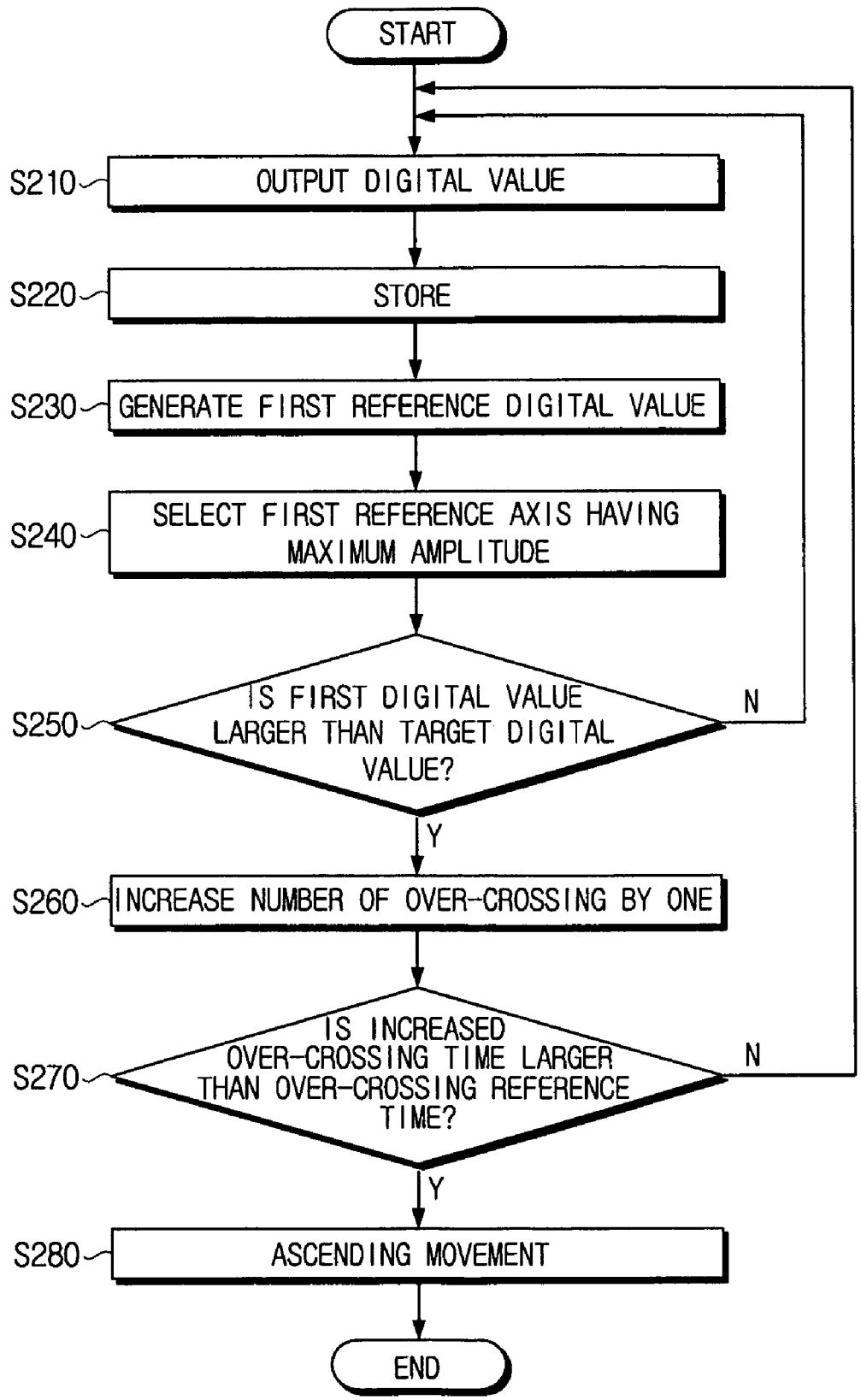
FIG. 2 is a flowchart showing a method of measuring an ascending movement of a footstep according to an exemplary embodiment of the present invention.

FIG. 2 is a flowchart showing a method of measuring the number of footsteps according to an exemplary embodiment of the present invention. Especially, the flowchart of FIG. 2 shows a method of measuring an ascending movement in the apparatus 100 shown in FIG. 1.

Referring to FIGS. 1 and 2, if a user moves after the user wears the apparatus 100 for measuring the number of footsteps, the terrestrial magnetism sensor 110 detects a (N−2) digital value at operation S210 and the output (N−2) digital value is stored at the memory 120 at operation S220. The terrestrial magnetism sensor 110 also detects a (N−1) digital value after one sampling time is elapsed after the (N−2) digital value is output at operation S210 and the output (N−1) digital value is stored in the memory 120 at operation S220. The terrestrial magnetism sensor 110 further detects an N digital value after one sampling time is elapsed after the (N−1) digital value is detected at operation S210 and the output N digital value is stored in the memory 120 at operation S220.

By using the stored (N−2) to N digital values, the digital value generator 130 generates a first reference digital value at operation S230. The first reference digital value may be generated according to Equation 1.

The reference axis selector 140 analyzes an X-axis digital value ($N_x$ digital value), a Y-axis digital value ($N_y$ digital value) and a Z-axis digital value ($N_z$ digital value) including the N digital value within a first predetermined period and selects a first reference axis having a maximum amplitude by finding a maximum value and a minimum value at operation S240.

Hereinafter, the first reference axis having the maximum amplitude is assumed as an X-axis.

The digital value determiner 150 compares the first reference digital value of the X axis and the $N_x$ digital value of the X axis at operation S250. The $N_x$ digital value is an N digital value of the X-axis and it may be represented as a target digital value.

If the first reference digital value is not larger than the $N_x$ digital value by a first predetermined value at operation S250, the operations S210 to S250 are repeatedly performed.

If the first reference digital value is larger than the $N_x$ digital value by a first predetermined value at operation S250, the counter increases the number of over-crossing by one at operation S260.

After increasing, the crossing time determiner 170 determines whether the increased over-crossing time is larger than an over-crossing reference time at operation S270.

If the increased over-crossing time is larger than the over-crossing reference time at operation S270, the controller 190 determines that a movement of the user is an ascending movement of one footstep at operation S280.

If the increased over-crossing time is smaller than the over-crossing reference time at operation S270, the operations S210 to S270 are repeatedly performed in response to the controller 190.

Figure 3:
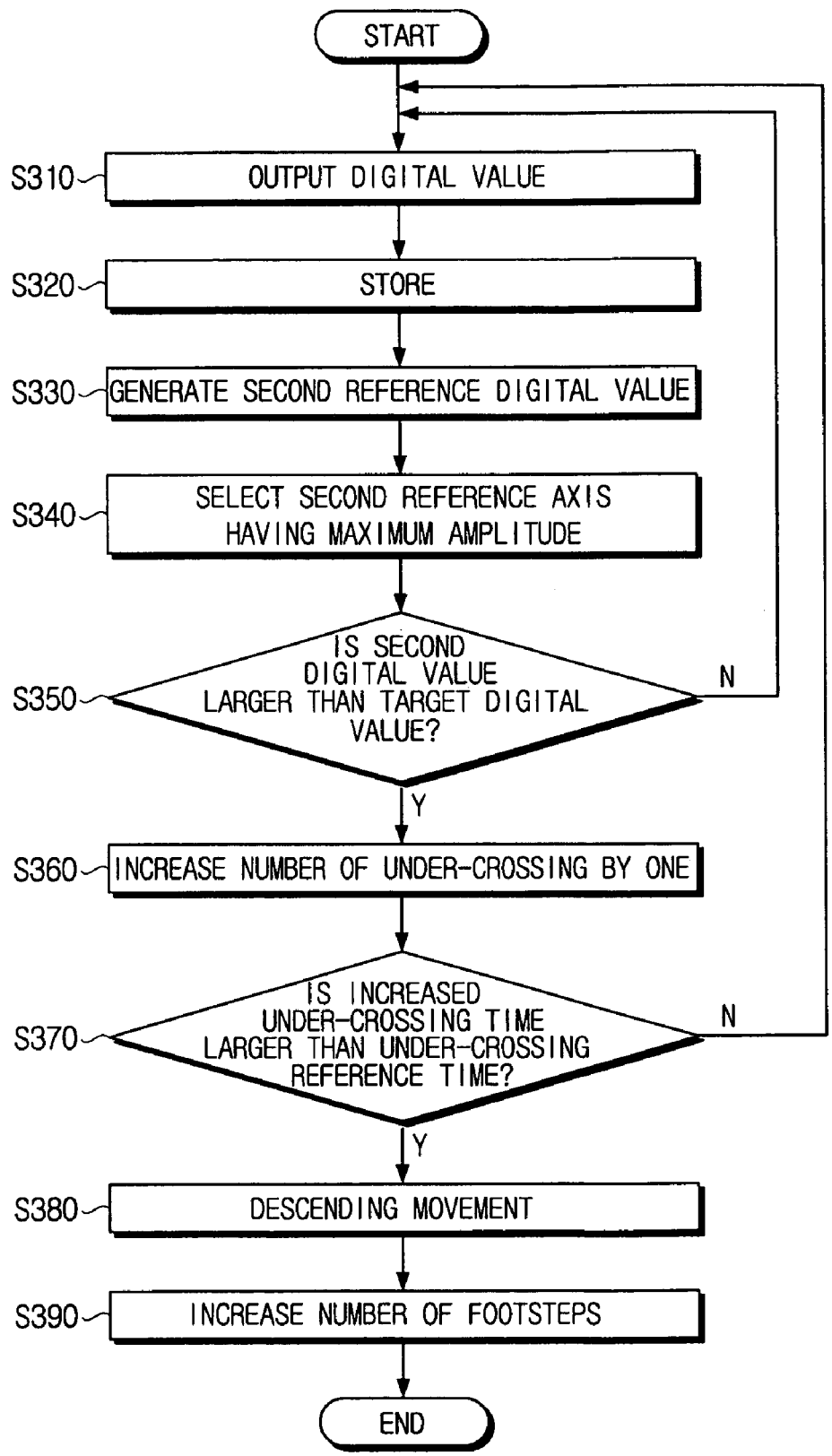
FIG. 3 is a flowchart showing a method of measuring a descending movement of a footstep according to an exemplary embodiment of the present invention.

FIG. 3 is a flowchart showing a method of measuring a descending movement in the apparatus shown in FIG. 1.

Referring to FIGS. 1 and 3, if the user continuously moves after the ascending movement of the user is detected, the terrestrial magnetism sensor 110 outputs a (N+k) digital value and a (N+k+1) digital value after one sampling time is elapsed after the (N+k) digital value is output at operation S310 and the output (N+k+1) digital value is stored in the memory 120 at operation S320. The terrestrial magnetism sensor 110 outputs a (N+k+2) digital value after one sampling time is elapsed after the (N+k+1) digital value is output at operation S310 and the output (N+k+2) digital value is stored in the memory 120 at operation S320. After one sampling time is elapsed after the (N+k+1) digital value is output, a (N+k+3) digital value is output at operation S310 and the output (N+k+3) digital value is stored in the memory 120 at operation S320.

By using the stored (N+k+1) to (N+k+3) digital values, the digital value generator 130 generates a second reference digital value at operation S330.

The reference axis selector 140 analyzes an X-axis digital value (($N+k+3)_x$ digital value), a Y-axis digital value (($N+k+3)_y$ digital value) and a Z-axis digital value (($N+k+3)_z$ digital value) including the (N+k+3) digital value within a second predetermined period and selects a second reference axis having a maximum amplitude by finding a maximum value and a minimum value at operation S340.

Hereinafter, the first reference axis having the maximum amplitude is assumed to be a Y-axis.

The digital value determiner 150 compares the second reference digital value of the Y axis and the $(N+k+3)_y$ digital value of the Y axis at operation S350. The $(N+k+3)_y$ digital value is an (N+k+3) digital value for the Y-axis and it may be represented as a target digital value.

If the second reference digital value is not smaller than the $(N+k+3)_y$ digital value by a second predetermined value at operation S350, the operations S310 to S350 are repeatedly performed in response to the controller 190.

If the second reference digital value is smaller than the $(N+k+3)_y$ digital value by a second predetermined value at operation S350, the counter increases the number of under-crossing by one at operation S360.

After increasing, the crossing time determiner 170 determines whether the increased under-crossing time is larger than an under-crossing reference time at operation S370.

If the increased over-crossing time is larger than the under-crossing reference time at operation S370, the controller 190 determines that a movement of the user is a descending movement of one footstep at operation S380. The counter 160 also increases the number of footsteps by one at operation S390.

If the increased under-crossing time is smaller than the under-crossing reference time at operation S370, the operations S310 to S370 are repeatedly performed in response to the controller 190.

Figure 4:
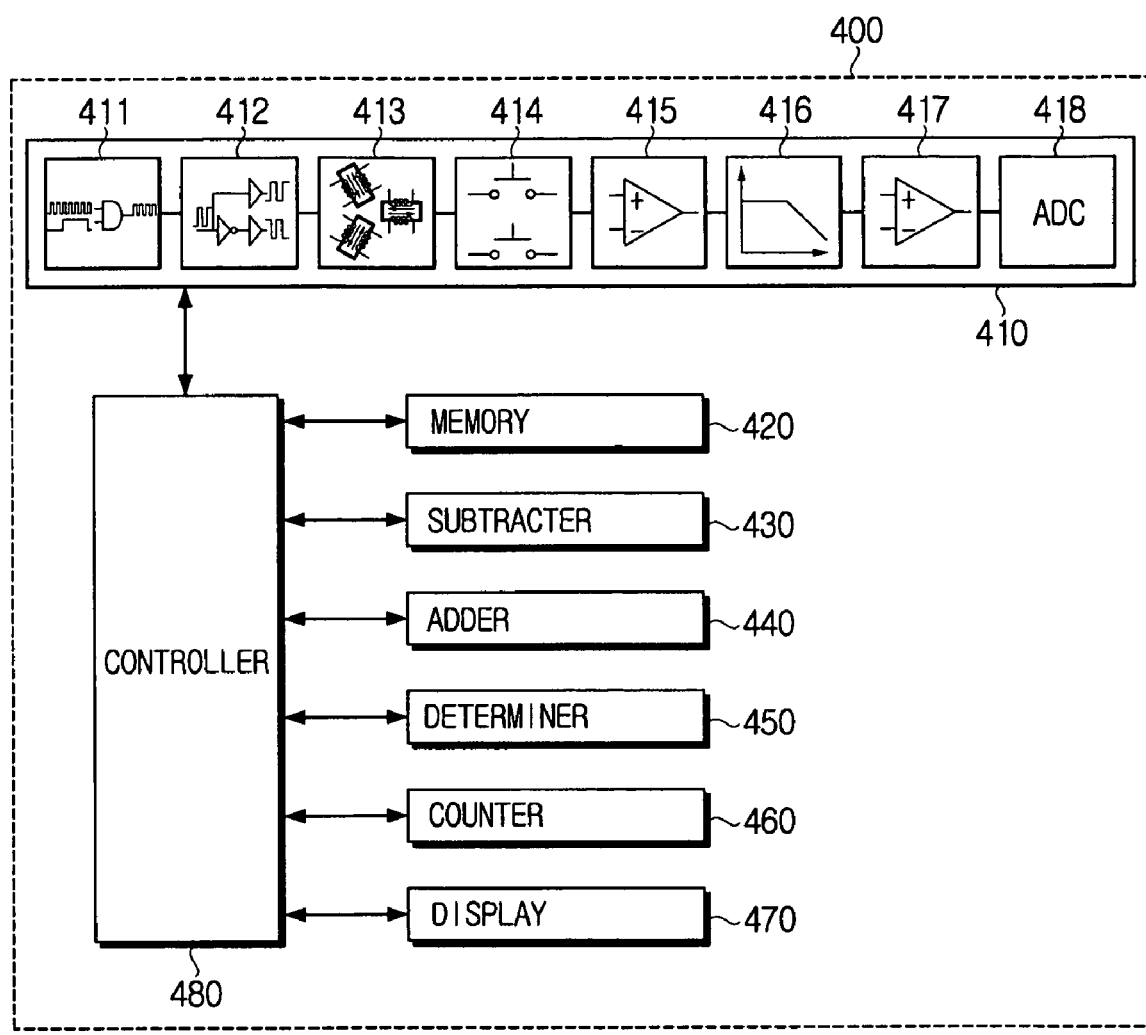
FIG. 4 is a block diagram illustrating an apparatus for measuring the number of footsteps according to another exemplary embodiment of the present invention.

FIG. 4 is a block diagram illustrating an apparatus for measuring the number of footsteps according to another exemplary embodiment of the present invention.

An apparatus 400 for measuring the number of footsteps according to another exemplary embodiment shown in FIG. 4 has elements similar to the apparatus 100 show in FIG. 1. Therefore, explanation of the similar elements of the apparatus 400 will be omitted to simplify the description of this embodiment.

Referring to FIG. 4, the apparatus 400 for measuring the number of footsteps according to another exemplary embodiment includes a terrestrial magnetism sensor 410, a memory 420, a subtracter 430, an adder 440, a determiner 450, a counter 460, a display 470 and a controller 480.

The terrestrial magnetism sensor 410 and the memory 420 perform similar functions of the terrestrial magnetism sensor 110 and the memory 120 shown in FIG. 1. The terrestrial magnetism sensor 410 outputs (M−1) digital values of each axis, such as an X-axis (M−1) digital value (($M−1)_x$ digital value), a Y-axis (M−1) digital value (($M−1)_y$ digital value) and a Z-axis (M−1) digital value (($M−1)_z$ digital value). After elapsing one sampling time interval after the (M−1) digital values are output, the terrestrial magnetism sensor 410 outputs M digital values of each axis such as an X-axis M digital value ($M_x$ digital value), a Y-axis M digital value ($M_y$ digital value) and a Z-axis M digital value (Mz digital value). The (M−1) digital values and the M digital values are stored in the memory 420 in response to the controller 480.

The subtracter 430 subtracts the (M−1) digital values from the M digital values according to each axis and calculates difference values of each axis (ΔX, ΔY, ΔZ) based on the subtraction results.

The adder 440 adds the difference values of each axis (ΔX, ΔY, ΔZ) and outputs a sum of the difference values.

The determiner 450 determines whether a zero-crossing has occurred, where the zero-crossing represents that the sum is transferred from a positive value to a negative value or vice versa. If the zero-crossing has occurred, the controller 480 determines that a movement of the user is a half of one footstep.

The counter 460 increases the number of zero-crossing by one when the zero-crossing has occurred. The counter 460 increases the number of footsteps by one when the number of the zero-crossing is 2. Meanwhile, the counter 460 is initialized by the controller 480 when the number of the zero-crossing is 2.

The display 470 displays the increased number of footsteps when the counter 460 increases the number of footsteps by one.

The controller 480 determines whether the increased number of zero-crossing is 2. If the increased number of zero-crossing is 2, the controller 480 determines that the movement of the user is one footstep.

Figure 5:
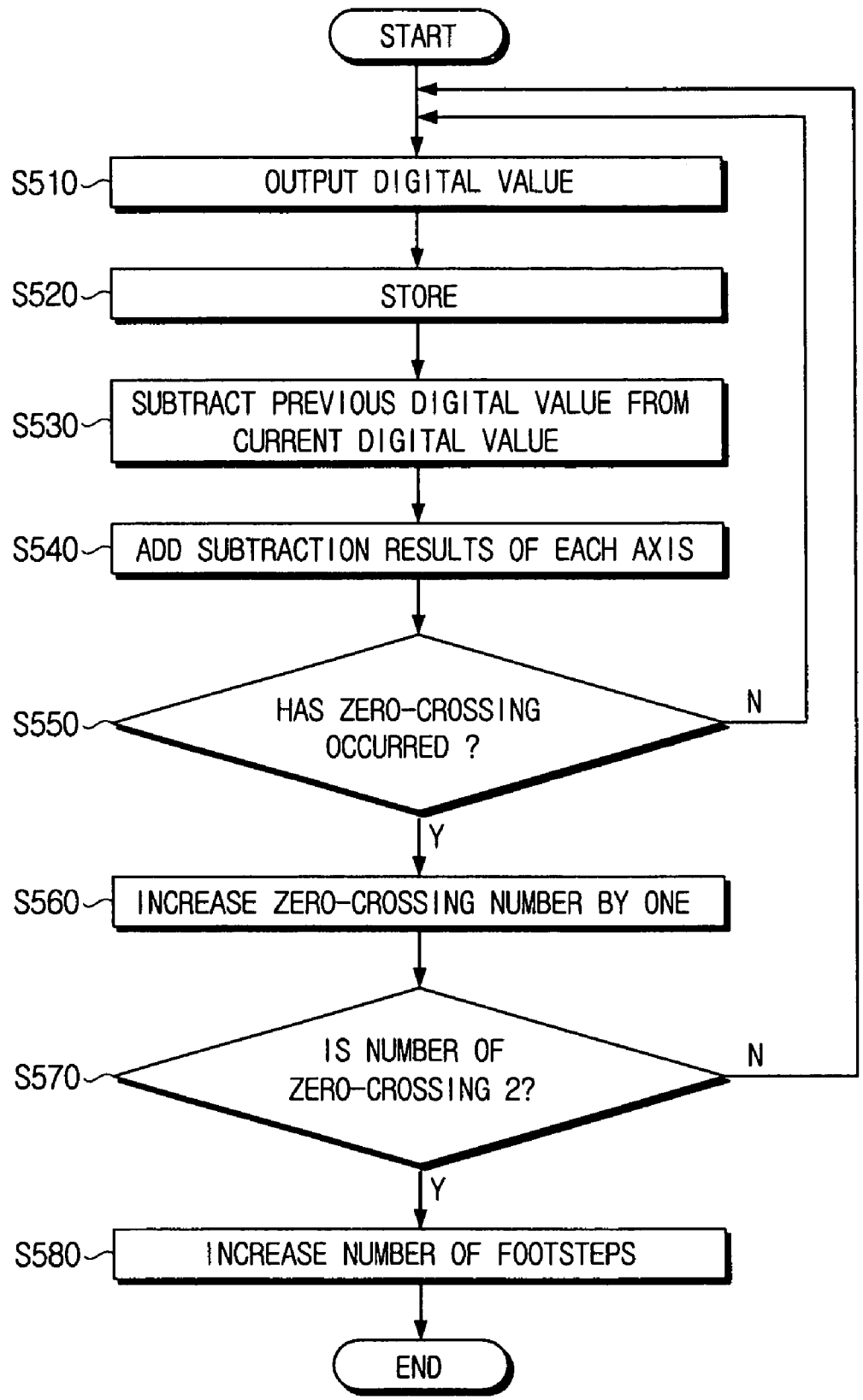
FIG. 5 is a flowchart showing a method of measuring the number of footsteps according to another exemplary embodiment of the present invention.

FIG. 5 is a flowchart showing a method of measuring the number of footsteps according to another exemplary embodiment of the present invention.

Referring to FIGS. 4 and 5, if a user moves after the user wears or equips the apparatus 400, (M−1) digital values of each axis are generated at operation S510. That is, the terrestrial magnetism sensor 410 generates an X-axis (M−1) digital value ((M−1)$_x$ digital value), a Y-axis (M−1) digital value ((M−1)$_y$ digital value) and a Z-axis (M−1) digital value ((M−1)$_z$ digital value) at operation S510. And, the output (M−1) digital values of each axis are stored in the memory 420 at operation S520. After outputting the (M−1) digital values and elapsing one sampling time, M digital values of each axis such as an X-axis M digital value (M$_x$ digital value), a Y-axis M digital value (My digital value) and a Z-axis M digital value (M$_z$ digital value) are output at operation S510 and the output M digital values are stored in the memory 420 at operation S520.

The subtracter 430 calculates difference values of each axis (ΔX, ΔY, ΔZ) by subtracting the (M−1) digital values of each axis from the M digital values of each axis at operation S530.

The adder 440 adds the calculated difference values (ΔX, ΔY, ΔZ) to output a sum of the difference values at operation S540.

The determiner 450 determines whether a zero-crossing has occurred at operation S550. That is, the determiner 450 determines whether the sum digital value is transferred from a positive value to a negative value or vice versa at operation S550.

If the zero-crossing has occurred at operation S550, the controller 480 determines that the movement of the user is a half of one footstep and the counter 460 increases the number of zero-crossing by one in response to the controller 480 at operation S560.

The controller 480 determines whether the increased number of zero-crossing is 2 at operation S570. If the increased number of zero-crossing is 2, the controller 480 determines that the movement of the user is one footstep at operation S580. The controller 480 increases the number of the footsteps by one. Meanwhile, the controller 480 initializes the number of the zero-crossing in the counter 460.

If the zero-crossing has not occurred, the controller 480 repeatedly performs the operations 510 through 570.

According to the present exemplary embodiments, a user may wear the apparatus 100 or 400 on the user's arm. This is because the terrestrial magnetism sensor 110 or 410 can generate a digital value according to a rotation angle formed by rotating the arm about the user's shoulder.

Also, according to the present exemplary embodiments, the user may wear the apparatus 100 or 400 on the user's leg. This is because the terrestrial magnetism sensor 110 or 410 can generate a digital value according to a rotation angle made by rotating the leg about a pelvis.

As described above, in the present exemplary embodiments, the terrestrial magnetism sensor is used for measuring the number of footsteps instead of using an acceleration sensor. Accordingly, the apparatus for measuring the number of footsteps using the terrestrial magnetism sensor according to the present exemplary embodiments consumes less electric power that a conventional apparatus for measuring the number of footsteps using the acceleration sensor. Therefore, the apparatus according to the present exemplary embodiments may be used longer than the conventional apparatus with a limited power source. Furthermore, the number of footsteps may be measured by considering noise in the present exemplary embodiments. Therefore, the number of footsteps may be precisely measured.

The foregoing embodiments are merely exemplary and are not to be construed as limiting the present invention. The present teachings can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. An apparatus for measuring a number of footsteps, the apparatus comprising:
    a terrestrial magnetism sensing unit which outputs digital values of at least two of an X-axis, a Y-axis and a Z-axis, within a predetermined sampling time interval according to movement of a body;
    a reference digital value generator which generates a reference digital value based on N digital values of each axis output from the terrestrial magnetism sensing unit, (N−1) digital values of each axis output from the terrestrial magnetism sensing unit in one sampling time interval before the N digital values are output, and (N−2) digital values of each axis output from the terrestrial magnetism sensor in one sampling time interval before the (N−1) digital values output;
    a reference axis selector which searches for an N digital value of an axis having a maximum amplitude in a predetermined period among the N digital values of each axis output and selects an axis having the maximum amplitude as a reference axis;
    a digital value determiner which determines whether the N digital value of the reference axis is larger than a reference digital value of the reference axis by a predetermined value; and
    a controller which determines the movement of the body is an ascending movement of one footstep, if the N digital value is larger than the reference digital value by a predetermined value.

2. The apparatus of claim 1, wherein the reference digital value generator generates the reference digital value (Ref$_{13}$ Value) based on the following equation:

$$Ref\_Value = a \times N\_RxF + b \times (N-1)\_RxF + c \times (N-2)\_RxF,$$

where N_RxF is an N digital value, (N−1)_RxF is a (N−1) digital value, the (N−2)_RxF is a (N−2) digital value, a denotes a weight allocated at an N sampling point, b represents a weight allocated at an (N−1) sampling point and c denotes a weight allocated at an (N−2) sampling point.

3. The apparatus of claim 1, wherein the controller determines that the movement of the body is a descending movement of one footstep when the digital value determiner determines that the N digital value of the reference axis is smaller than the reference digital value of the reference axis by a predetermined value.

4. The apparatus of claim 3, further comprising:
a counter which increases the number of footsteps by one if the controller determines the movement of the body is the descending movement.

5. The apparatus of claim 4, further comprising:
a display which displays the number of footsteps counted by the counter in response to the controller.

6. The apparatus of claim 1, wherein the terrestrial magnetism sensing unit comprises a two-axis fluxgate circuit or a three-axis fluxgate circuit that is configured to detect the movement of the body.

7. An apparatus for measuring a number of footsteps, the apparatus comprising:
a terrestrial magnetism sensing unit which outputs digital values of at least two of an X-axis, a Y-axis and a Z-axis, within a predetermined sampling time according to movement of a body;
a subtracter which generates difference digital values of each axis output by subtracting (N−1) digital values, which are output in one sampling time before outputting N digital values from the terrestrial magnetism sensing unit, from the N digital values of each axis which are output;
an adder which generates a sum digital value by adding the difference values of each axis output; and
a controller which determines that the movement of the body is a half of one footstep if a sign of the sum digital value is changed.

8. The apparatus of claim 7, wherein the controller determines that the movement of the body is another half of one footstep when the sign of the sum digital value, which was changed, is changed again.

9. The apparatus of claim 8, further comprising:
a counter which increases the number of footsteps by one if the controller determines that the movement of the body is another half of one step.

10. The apparatus of claim 9, further comprising a display which displays the number of footsteps counted by the counter in response to the controller.

11. The apparatus of claim 7, wherein the terrestrial magnetism sensing unit comprises a two-axis fluxgate circuit or a three-axis fluxgate circuit that is configured to detect the movement of the body.

12. A method of measuring a number of footsteps, the method comprising:
outputting digital values of at least two of an X-axis, a Y-axis and a Z-axis of a terrestrial magnetism sensor according to movement of a body;
generating a reference digital value based on N digital value of each axis which is output, (N−1) digital values of each axis output in a sampling time before outputting the N digital values, and (N−2) digital values of each axis output in a sampling time before outputting the (N−1) digital values;
searching an N digital value of an axis having a maximum amplitude in a predetermined period among the N digital values of each axis and selecting the axis having the maximum amplitude as a reference axis;
determining whether the N digital value of the reference axis is larger than a reference digital value of the reference axis by a predetermined value; and
determining that the movement of the body is an ascending movement of one footstep if the N digital value is larger than the reference digital value by a predetermined value.

13. The method of claim 12, wherein in the generating the reference digital value, the reference digital value (Ref_Value) is generated based on the following equation:

$$\text{Ref\_Value} = a \times N\_RxF + b \times (N-1)\_RxF + c \times (N-2)\_RxF,$$

where N_RxF is an N digital value, (N−1)_RxF is a (N−1) digital value, the (N−2)_RxF is a (N−2) digital value, a denotes a weight allocated at an N sampling point, b represents a weight allocated at the (N−1) sampling point and c denotes a weight allocated at the (N−2) sampling point.

14. The method of claim 12, further comprising: determining that the movement of the body is a descending movement of one footstep if it is determined that the N digital value of the reference axis is a predetermined value smaller than the reference digital value of the reference axis.

15. The method of claim 14, further comprising: increasing the number of footsteps by one if the movement is determined to be the descending movement.

16. The method of claim 15, further comprising: displaying a number of counted footsteps.

17. The method of claim 12, wherein the terrestrial magnetism sensing unit comprises a two-axis fluxgate circuit or a three-axis fluxgate circuit that detects the movement of the body.

18. A method for measuring a number of footsteps, the method comprising:
outputting digital values of at least two of an X-axis, a Y-axis and a Z-axis using a terrestrial magnetism sensor according to movement of a body;
generating difference digital values of each axis which is output by subtracting (N−1) digital values, which are output in one sampling time before outputting N digital values, from the N digital values of each axis which is output;
generating a sum digital value by adding the difference digital values of each axis which is output; and
determining that the movement of the body is a half of one footstep if a sign of the sum digital value is changed.

19. The method of claim 18, further comprising determining that the movement of a body is another half of one footstep if the sign of the sum digital value, which is changed, is changed again.

20. The method of claim 19, further comprising: increasing the number of footsteps by one if it is determined that the movement of the body is another half of one step.

21. The method of claim 20, further comprising: displaying a number of counted footsteps.

22. The method of claim 18, wherein the terrestrial magnetism sensing unit comprises a two-axis fluxgate circuit or a three-axis fluxgate circuit that detects the movement of the body.

* * * * *